US005585068A

United States Patent [19]

Panetz et al.

[11] Patent Number: 5,585,068

[45] Date of Patent: Dec. 17, 1996

[54] APPARATUS FOR AUTOMATICALLY SEPARATING A COMPOUND FROM A PLURALITY OF DISCRETE LIQUID SPECIMENS

[75] Inventors: Allen I. Panetz, St. James; Richard D. Gordon, Sayville; Mohammad A. Farooqi, Brentwood; Guy A. Cosmo, So. Setauket; Nicholas Cosmo, Garden City Park, all of N.Y.

[73] Assignee: BioChemical Diagnostics, Inc., Brentwood, N.Y.

[21] Appl. No.: 323,240

[22] Filed: Oct. 14, 1994

Related U.S. Application Data

[63] Continuation of Ser. No. 916,602, Jul. 20, 1992, abandoned, which is a continuation-in-part of Ser. No. 483,110, Feb. 20, 1990, abandoned.

[51] Int. Cl.$^6$ .................................................... G01N 21/01

[52] U.S. Cl. ................................ 422/64; 422/63; 422/65; 422/67; 422/69; 422/70; 422/100; 422/101; 422/104; 73/864.91; 436/47; 436/177; 436/178

[58] Field of Search .................... 73/864.91; 422/63–67, 422/69, 70, 100, 101, 104; 436/47, 174, 177, 178

[56] References Cited

U.S. PATENT DOCUMENTS

| | | | |
|---|---|---|---|
| 2,566,430 | 9/1951 | Sobers | 422/104 |
| 3,193,359 | 7/1965 | Baruch | 422/65 |
| 3,219,416 | 11/1965 | Natelson | 422/64 |
| 3,443,439 | 5/1969 | Cruz | 73/863.32 |
| 3,522,011 | 7/1970 | Sanderson | 422/65 |
| 3,536,452 | 10/1970 | Norton et al. | 422/63 |
| 3,575,692 | 4/1971 | Gilford | 422/65 |
| 3,578,412 | 5/1971 | Martin | 422/65 |
| 3,583,230 | 6/1971 | Patterson | 422/70 X |
| 3,625,652 | 12/1971 | Fujimoto et al. | 422/69 X |
| 3,712,144 | 1/1973 | Kuzel et al. | 422/64 X |
| 3,753,657 | 8/1973 | Downing et al. | 422/65 |
| 3,768,526 | 10/1973 | Sanz et al. | 422/63 |
| 3,832,135 | 8/1974 | Drozdowski et al. | 422/65 X |
| 3,847,200 | 11/1974 | Kopp et al. | 422/206 |
| 3,901,656 | 8/1975 | Durkos et al. | 422/64 |
| 3,966,410 | 6/1976 | Jahnsen | 436/178 |
| 4,003,713 | 1/1977 | Bowser | 422/101 |
| 4,077,444 | 3/1978 | Gilson et al. | 422/65 |
| 4,155,711 | 5/1979 | Zelagin et al. | 422/65 |
| 4,160,803 | 7/1979 | Potts | 422/101 |
| 4,186,187 | 1/1980 | Jahnsen | 422/64 |
| 4,198,483 | 4/1980 | Sogi et al. | 422/63 X |
| 4,219,530 | 8/1980 | Kopp et al. | 422/101 |
| 4,221,568 | 9/1980 | Boettger | 422/64 |
| 4,234,317 | 11/1980 | Lucas et al. | 422/101 |
| 4,259,290 | 3/1981 | Suovaniemi et al. | 422/65 |

(List continued on next page.)

FOREIGN PATENT DOCUMENTS 0212663 3/1987 European Pat. Off. .

OTHER PUBLICATIONS

M. S. Roginsky et al. *Clin. Chim. Acta* 1975, 63, 303–308.
Fisher Catalog 1988 pp. 259 and 936–939.
Fisher Catalog copyright 1990 p. 310.

*Primary Examiner*—Jill Warden
*Assistant Examiner*—Arlen Soderquist
*Attorney, Agent, or Firm*—Galgano & Burke

[57] ABSTRACT

An apparatus for automatically separating at least one compound from a plurality of discrete liquid specimens. One embodiment utilizes sample preparation columns which are automatically fed to a column transport disc. The transport disc is preferably provided with compound bores which allow the columns to be easily positioned, transported past a plurality of reagent/gas dispense stations, and ejected after use. Another aspect of a preferred embodiment provides for separate dispensing of reagent and pressurized gas into the sample preparation columns. Eluate is preferably collected in containers. In order to enhance the drying of the eluate collection containers, heated gas, e.g. air, can be directed into the containers. Alternatively, the eluate containers can be heated and vented to enhance drying.

26 Claims, 11 Drawing Sheets

U.S. PATENT DOCUMENTS

| | | | |
|---|---|---|---|
| 4,260,581 | 4/1981 | Sakuvada | 422/66 X |
| 4,276,260 | 6/1981 | Drbal et al. | 422/64 |
| 4,279,860 | 7/1981 | Smolen | 422/100 |
| 4,287,155 | 9/1981 | Tersteeg et al. | 422/64 |
| 4,301,116 | 11/1981 | Ida et al. . | |
| 4,338,280 | 7/1982 | Ambers et al. | 422/68.1 |
| 4,406,547 | 9/1983 | Aihara | 422/64 X |
| 4,497,711 | 2/1985 | Shepherd | 210/656 |
| 4,499,053 | 2/1985 | Jones | 422/68.1 |
| 4,559,201 | 12/1985 | Yamada et al. | 422/104 X |
| 4,600,473 | 7/1986 | Friswell | 422/101 X |
| 4,681,742 | 7/1987 | Johnson et al. | 422/65 |
| 4,707,452 | 11/1987 | Friswell | 436/177 |
| 4,711,764 | 12/1987 | Good | 422/65 |
| 4,751,186 | 6/1988 | Baisch et al. | 422/65 |
| 4,766,082 | 8/1988 | Marteau D'Autry | 422/65 |
| 4,797,258 | 1/1989 | Mochida | 422/65 |
| 4,798,095 | 1/1989 | Itoh | 422/63 |
| 4,803,050 | 2/1989 | Mack | 422/65 |
| 4,806,487 | 2/1989 | Akers et al. | 436/178 X |
| 4,810,471 | 3/1989 | Wachob et al. | 436/178 X |
| 4,824,641 | 4/1989 | Williams | 422/65 X |
| 4,837,159 | 6/1989 | Yamada | 422/67 X |
| 4,844,868 | 7/1989 | Rokugawa | 422/65 |
| 4,849,176 | 7/1989 | Sakagami | 422/65 |
| 4,858,155 | 8/1989 | Okawa et al. | 422/63 X |
| 4,906,432 | 3/1990 | Geiselman | 422/100 |
| 4,927,765 | 5/1990 | Saxon et al. | 422/100 |
| 4,948,563 | 8/1990 | Kanewske, III | 422/99 |
| 4,956,148 | 9/1990 | Grandone | 422/64 |
| 4,965,049 | 10/1990 | Lillig et al. | 422/67 |
| 4,971,913 | 11/1990 | Manabe et al. | 422/67 |
| 5,008,082 | 4/1991 | Shaw | 422/65 |
| 5,045,208 | 9/1991 | Sanford et al. | 422/70 X |
| 5,100,623 | 3/1992 | Friswell | 436/177 X |

APPARATUS FOR AUTOMATICALLY SEPARATING A COMPOUND FROM A PLURALITY OF DISCRETE LIQUID SPECIMENS

This is a continuation of application Ser. No. 07/916,602 filed on Jul. 20, 1992, now abandoned, which, in turn, is a continuation-in-part of Ser. No. 07/483,110, filed Feb. 20, 1990, which is now abandoned.

The present invention is directed to a method and apparatus for filtering or extracting constituents from solutions or solids and, more particularly, to an apparatus and method for the preparation of test samples wherein at least one compound is separated from a plurality of discrete liquid specimens, such as body fluids, environmental samples or pharmaceutical preparations, for subsequent analysis.

BACKGROUND OF THE INVENTION

Methods for the analysis of fluids, particularly body fluids, for the presence and quantity of solutes have been known for many years. Recently, an increased desire for the analysis of body fluids for substances, such as steroids and narcotics, has greatly increased the demand for urine analysis. The greater number of samples which need to be tested has created a need for automated analysis procedures which retain at least as much accuracy and reproducibility as conventional methods.

One conventional method of urine analysis comprises contacting a urine specimen with an adsorbent material capable of adsorbing the specific solute in question. For example, a predetermined quantity of adsorbent is placed in a column having openings at both the top and bottom. The adsorbent is held in place by frits, i.e., small plastic screens, which are inert with respect to the materials used in the test procedure. Before introducing the specimen to the test column, the adsorbent is typically cleaned by flushing the column with water or another suitable reagent. The surface of the adsorbent may also be prepared for the specimen by passing one or more reagents through the column. This preparation treatment provides the surface of the adsorbent with a greater affinity for the solute which is being removed from the urine specimen. After the adsorbent has been properly prepared, the specimen is introduced into the column. Since the degree of adsorption of solute by the adsorbent may be highly time-dependent, it is common practice to control the time that the specimen is in contact with the adsorbent by providing a positive pressure at the top of the column or by providing a vacuum at the bottom of the column after the specimen has been introduced into the test column.

Various devices have been disclosed for preparing test samples for analysis. Many of these devices operate in a "batch" manner wherein a number of test samples (a first batch) are placed into a device which performs a first step of a sample preparation procedure on each sample, often one at a time, and then performs a second step on each sample, etc. until the sample preparation procedure has been completed. A laboratory technician then removes the first batch and places a second batch of test samples into the device. Such "batch" devices typically result in a substantial amount of waiting time by laboratory personnel. Furthermore, the "batch" preparation of a large number of test samples using a corresponding number of sample preparation devices, creates the risk of mismatching the collected eluates and test samples.

These disadvantages can be overcome by a method and apparatus for sample preparation which provides the option of processing test samples on a continuous or batch basis.

Known apparatus for preparing and/or analyzing test specimens which operate on a batch basis are typically designed to perform a procedural step on only one of the given specimens at a time, to have the same number of receptacles as specimens in the batch, and to require time consuming modifications for different sized sample preparation devices. Therefore, in order to process a large batch of test specimens in a single run, such apparatus had to be relatively large.

It is, therefore, desirable to provide a smaller, compact sample preparation apparatus which can prepare samples for further analysis on either a batch or continuous basis.

It is also desirable to provide an apparatus which is easily adapted for use with sample preparation devices of different sizes.

SUMMARY OF THE INVENTION

One aspect of the present invention provides a mechanism for automatically feeding sample preparation columns to a transport mechanism. In the transport mechanism, the sample preparation columns are transported to a number of reagent dispensing stations where they are prepared to receive a test specimen. After preparation, a test specimen is delivered to the sample preparation column utilizing a disposable transfer tip. Those skilled in the art will appreciate that the use of a disposable transfer tip provides greater test integrity by minimizing the risk of contamination between test specimens.

The present invention also provides the option of automatically collecting the portion of the test specimen or other eluates exiting from the bottom of the column. Such collections can be selectively performed at one or more stations along the transport path. Otherwise fluids exiting the columns at the various stations may be diverted to waste containers.

After passing the test specimen through the sample preparation column, the column is transported to additional stations for further preparation and collection of eluate.

The transport mechanism of the present invention illustrated herein is advantageously circular and is provided, not only with the above-described column feeding mechanism, but also with a column ejector. The column ejector clears the transport mechanism of used columns thereby creating space for fresh columns which are used in the preparation of additional samples. By providing an apparatus which automatically feeds fresh columns and ejects used columns from the transport mechanism, the apparatus of the present invention allows for greater utilization of a smaller apparatus within a laboratory and also provides a mechanism for either continuous or batch preparation of test specimens.

Another aspect of the present invention allows for the use of sample preparation columns of any size. Those skilled in the art will appreciate that different size columns are common in the industry. Therefore, by providing a single apparatus adapted for use with different size columns, valuable laboratory space and resources can be utilized to their greatest efficiency.

Another aspect of the present invention further decreases the risk of contamination between test specimens as well as different reagents used for different test procedures by effectively providing separate stations for the dispensing of reagent and pressurized gases to the sample preparation columns.

Thus the present invention is particularly advantageous in circumstances wherein it is desirable to save a test specimen which has been passed through a sample preparation column and where it is also necessary to collect eluate flowing from the exit port at a different station. These and other advantages will become apparent to those skilled in the art from the drawings and description set forth below.

DETAILED DESCRIPTION

The present invention is capable of separating at least one compound from a plurality of discrete liquid specimens with minimal intervention required from a lab technician. The apparatus of the present invention is capable of automatically removing at least one compound from a plurality of discrete liquid specimens, for example cocaine from urine specimens, in a manner which is quicker and provides greater reliability than a laboratory technician working manually.

Figure 1:
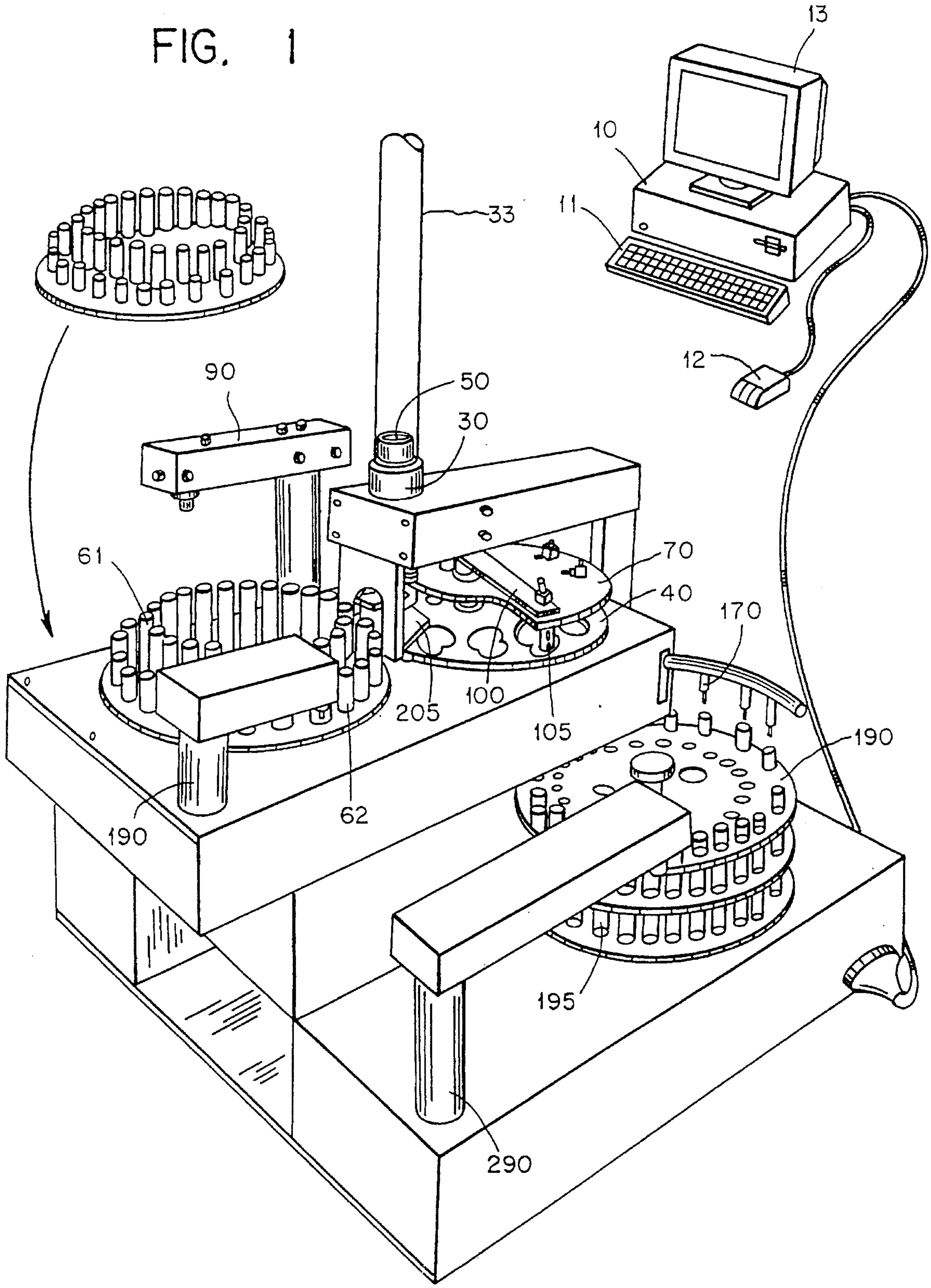
FIG. 1 is a perspective view of one embodiment of the present invention.

The illustrated embodiment of the present invention, as shown in FIG. 1, is advantageously provided with a control and monitoring system including a central processing unit 10, a keyboard 11, a mouse 12, and a video monitor 13 which provide laboratory technicians with user-friendly controls for initiating and modifying a wide variety of sample preparation procedures. In addition to enabling the apparatus of the present invention to be readily programmed for a wide variety of sample preparation procedures, these controls also advantageously provide a number of safety and quality control checks.

This embodiment also comprises an automatic column feed mechanism 30 which delivers sample preparation columns 50 into a transport disc 40 which moves the columns 50 to twelve stations in stepwise fashion. The columns 50 are treated at these stations with reagents and/or pressurized gasses which are fed to the columns through reagent dispensers and pressurized gas dispensers. For example, various reagents are directed through the sample preparation columns 50 as desired for a given sample preparation procedure. After any necessary column preparation, a specimen transfer assembly 90 engages a disposable transfer tip 61 and utilizes that transfer tip 61 to transfer a test specimen from a specimen container 62 to a sample preparation column 50. Liquids flowing out the outlet port of the sample preparation columns 50 are either directed to one or more waste collection vessels or can be collected at desired stations in eluate collection tubes.

Figures 3, 4:
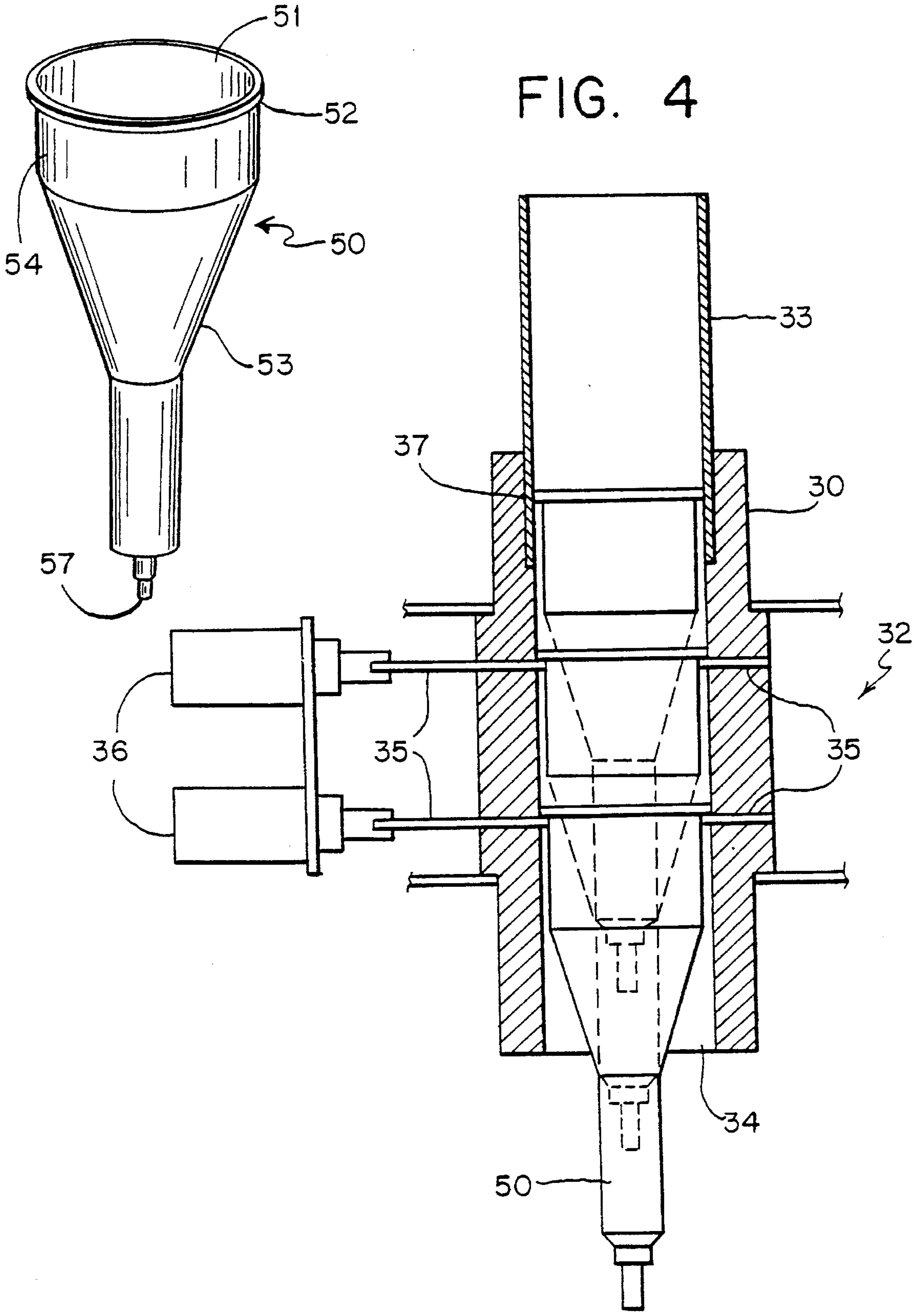
FIG. 3 is a side perspective view of a sample preparation column.
FIG. 4 is a cross-sectional, side view of col. feeder utilized with the apparatus illustrated in FIG. 1.

The sample preparation column 50, illustrated in the FIG. 3 is commonly available in the industry and is sold under the trademark Detectabuse™ Solid Phase Extraction Columns. As used herein, the term "sample preparation column" is meant to include any form of housing having an inlet port and an outlet port with some mechanical or chemical material for removing at least one substance from a fluid passing through the column. For example, included within the meaning of this term are solid phase extraction columns as well as filtration devices. For purposes of illustration, the illustrated embodiment of the present invention is described as using a solid phase extraction column 50 having a cylindrical upper sidewall 54 defining an inlet port 51 which is circumscribed by a flanged rim 52. A generally open, funnel-shaped body 53 extends downwardly from sidewall 54 and directs fluids into successively narrower passages until that fluid exits through outlet port 57. A chemical absorbent is advantageously disposed below the funnel-shaped body 53 and above outlet port 57 and can contain any suitable substance capable of performing the desired separation.

At the beginning of a test procedure, the control unit preferably runs the entire apparatus through a check procedure in order to insure that all of the mechanisms are functional and ready to perform a sample preparation procedure. The check procedure will advantageously insure that no columns have been left in transport disc 40 from a prior procedure and also that all moving elements are moving in an unobstructed fashion. A number of electrical sensors are strategically positioned at different locations on the apparatus for this purpose and are coupled to the central processing unit 10.

After the check procedure, a column is fed by a column feed mechanism to the column transport disc 40 at a location designated herein as task station one. Sample preparation columns 50 are initially loaded into a bulk load magazine 33 which is in the form of a cylindrical tube shown in FIG. 4. Bulk load magazine 33 is also preferably formed of a transparent material, such as cellulose acetate, in order to allow laboratory personnel to readily monitor the number of columns available for feeding to transport disc 40. The configuration of columns 50 advantageously allows the columns to be nestled within the bulk load magazine 33 in vertical, overlapping arrangement in order to conserve space.

The column feed mechanism 30 has a vertical, cylindrical chamber 34 with an inside diameter matching that of the bulk load magazine 33 and having a counterbore 37 at its upper end, of adequate diameter and depth to accept and support the outside diameter of the lower, discharge end of the bulk load magazine 33.

Figure 5:
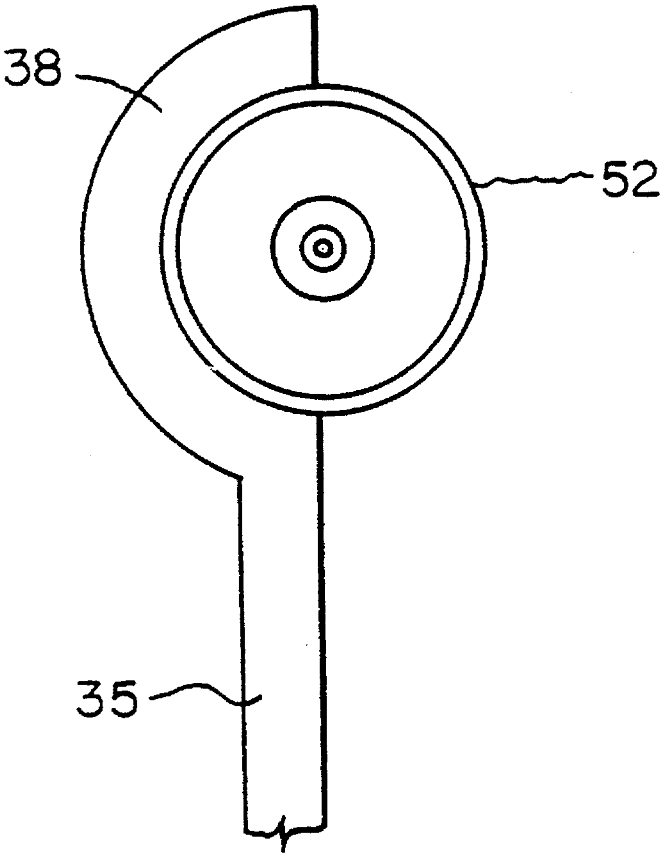
FIG. 5 is a top view of an actuator arm and a sample preparation column.

The delivery of columns 50 is controlled by a pair of independently operable electric actuating mechanisms 36 and actuator arms 35. As shown in FIG. 5, actuator arms 35 are formed with a semi-circular gripping portion 38 having an internal diameter slightly smaller than the rim flange 52 and slightly larger than the generally cylindrical portion 54 of a column 50. Thus when actuator arm 35 is located within the path of columns 50, rim flange 52 abuts the gripping portion 38 of actuator arm 35 thereby stopping the descent of that column 50. From FIG. 4, it can therefore be readily appreciated that the bottom column in the column feed mechanism can be dropped into the column transport mechanism 40 by simply sending a signal to the lower actuator 36 which moves lower actuator arm 35 out of the path of rim flange 52 of that lowest column 50. The lowest column is then permitted to fall freely into transport disc 40. The lower actuator 36 is then signaled to return lower actuator arm 35 to its normally "closed" position where lower actuator arm 35 is then again ready to stop another column 50. With lower actuator arm 35 back in its normally "closed" position, a signal is then sent to open upper actuator arm 35 in the same manner thereby allowing the columns 50 within the bulk load magazine 33 to descend until the lowest column abuts the lower actuator arm 35.

In this manner, sample preparation columns can be readily delivered to the column transport disc 40 without operator intervention. As a further time saving step for laboratory personnel, the present invention allows bulk load magazine 33 to be refilled through an opening in the top of the magazine when the number of fresh columns in the magazine 33 is observed to be getting low. Alternatively, a manufacturer of columns can readily package a predetermined number of sample preparation columns 50 in a disposable magazine which laboratory personnel can readily load into column feed mechanism 30.

An opto-electrical sensor (not shown) is positioned to detect the presence or absence of a column in the transport disc 40 at task station one and verifies the proper operation of the column feed mechanism 30.

Figure 6:
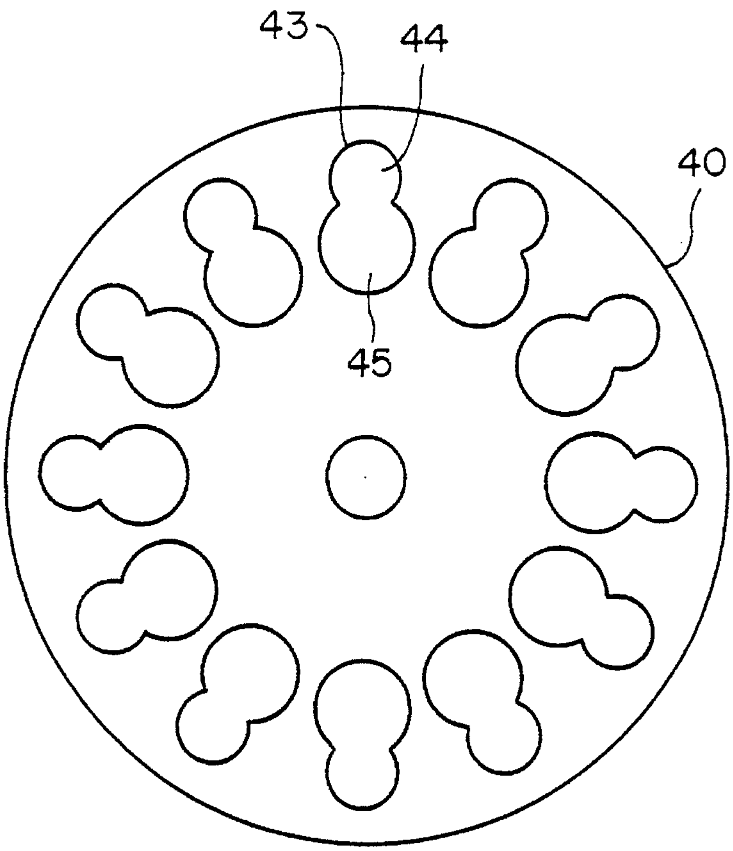
FIG. 6 is a top view of a column transport disc. utilized with the apparatus illustrated in FIG. 1.

With reference to FIG. 6, the rotatable transport disc 40 of the illustrated embodiment is disposed in the horizontal plane with twelve compound bores 43 spaced at intervals of about 30 degrees. Each compound bore 43 has a support section 44 with a minor diameter and a release section 45 with a major diameter. Each compound bore 43 is configured to support one sample preparation column 50 in the support section 44 as the column 50 is carried along the transport path to each of the task stations by the rotation of transport disc 40.

The rotation of transport disc 40 can be accomplished by any acceptable method known in the art. For example, a low voltage, electric transport motor may be equipped with a cogged driver pulley fixed to an output shaft and positioned to engage a cogged drive belt which acts in conjunction with a cogged driven pulley on a central support shaft attached to the transport disc 40. The transport motor may be energized after a column has been delivered to transport disc 40 at task station one to transport the column to station two. The motor may then be de-energized stopping that column and positioning an empty compound bore 43 under column feed mechanism 30 at task station one. This advancement of a column from one task station to the next is referred to herein as an INDEX. An opto-electrical sensor (not shown) is also advantageously positioned to detect the presence of a column in the transport path at task station two and to provide a control signal to de-energize the transport motor at the proper times to complete the index.

Once the column has been detected absent at task station one and subsequently present at task station two, by the opto-electrical sensors, the column feed mechanism 30 is signaled to deliver another column from the bulk load magazine 33 into the transport path at task station one.

The control and monitoring system controls the operation of the illustrated apparatus. Particularly, the central processing unit 10 is programmed to send carefully timed signals to the various mechanisms which deliver reagents, gasses and specimens to the sample preparation columns at the task stations. Therefore, if the sample preparation procedure requires the dispensing of a reagent into the column 50 at a task station, the reagent dispense and column pressurization system will be employed. Reagents and pressurizing gasses are delivered to sample preparation columns at the task stations through the cooperation of a pressure head 70 and a nozzle support rack 100.

Figure 13:
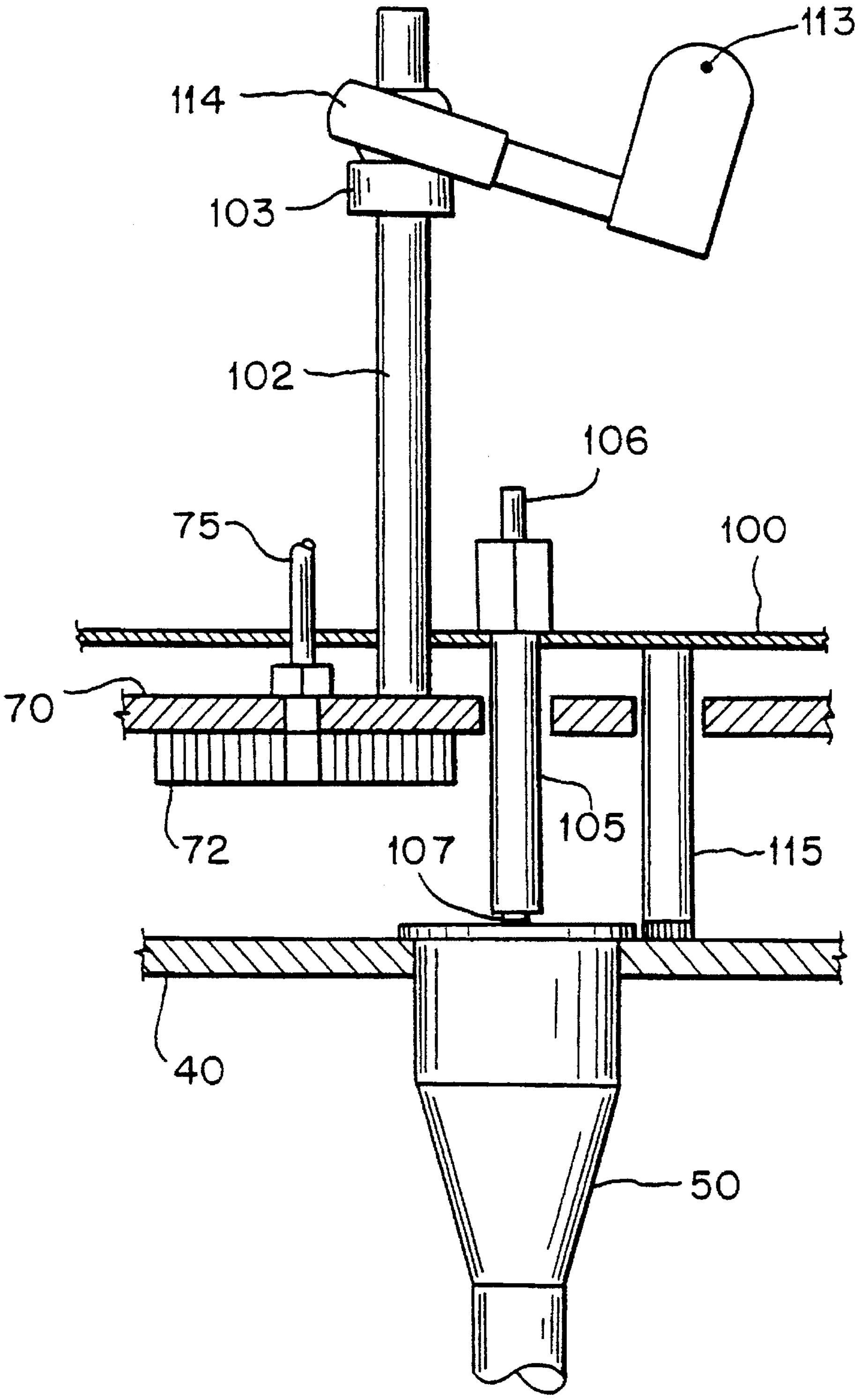
FIGS. 13 and 14 are perspective, side views of a pressure head shift mechanism of the embodiment of the present invention shown in FIG. 1.
Figure 14:
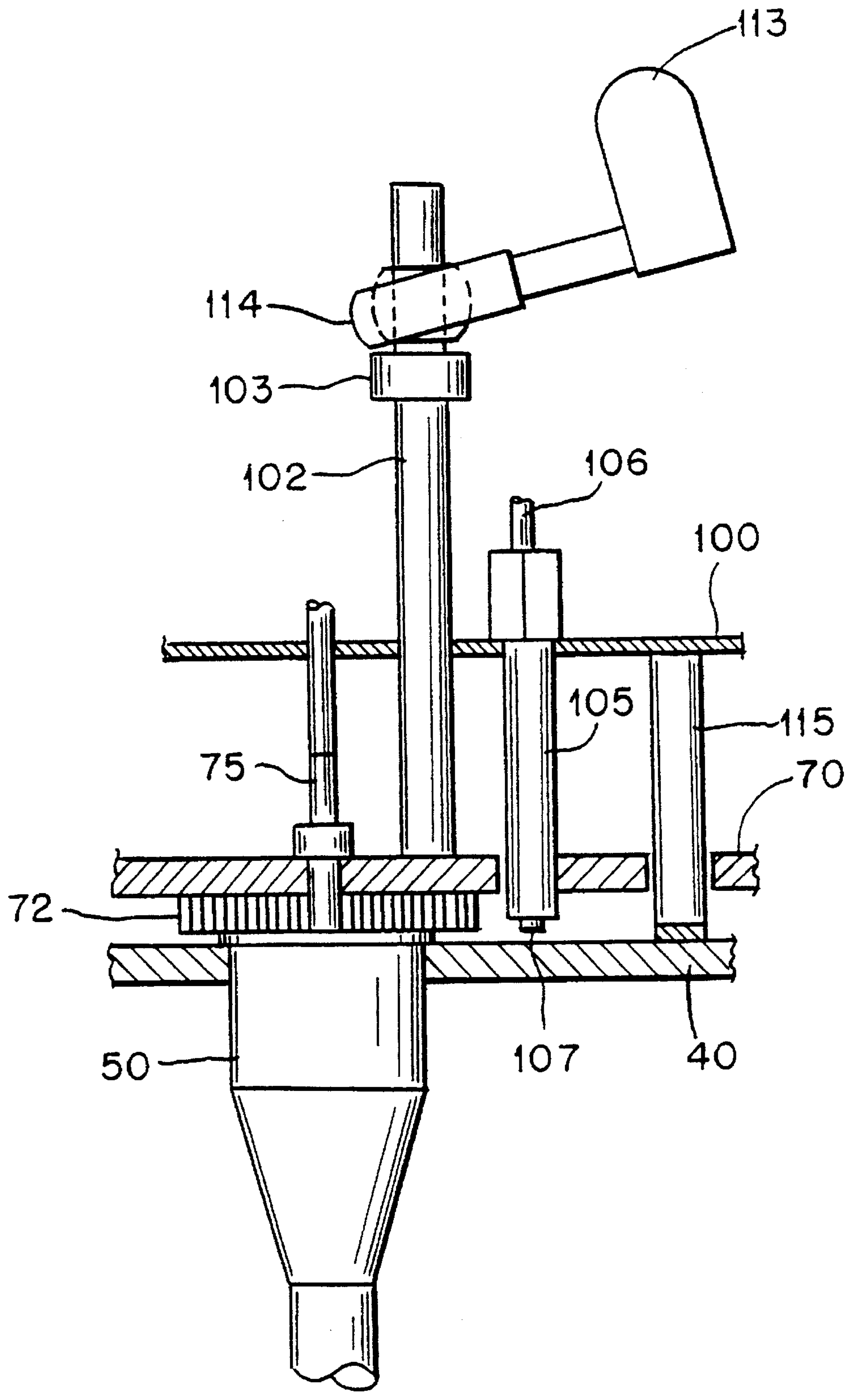

The illustrated embodiment of the present invention is designed to deliver reagent to sample preparation columns positioned at task stations two through six and ten, and to deliver pressurized gas at task stations two through ten. The reagent dispense and gas pressurization system of the illustrated apparatus is designed to supply a pressurized gas to one or more of the sample preparation columns 50 when the pressure head is lowered to a PRESSURIZE position, or to dispense reagent to one or more of the sample preparation columns 50 when the pressure head 70 is in a DISPENSE position. In order to avoid contamination between specimens, the present invention is also advantageously designed to keep the reagent dispense nozzles and the pressurization nozzles separate during the preparation procedure. In order to achieve this separation, the column pressurization nozzles 75 are rigidly attached to the pressure head 70 as shown in FIGS. 13 and 14. Neighboring pressurization nozzles are spaced about 30 degrees apart on the pressure head 70.

Figure 7:
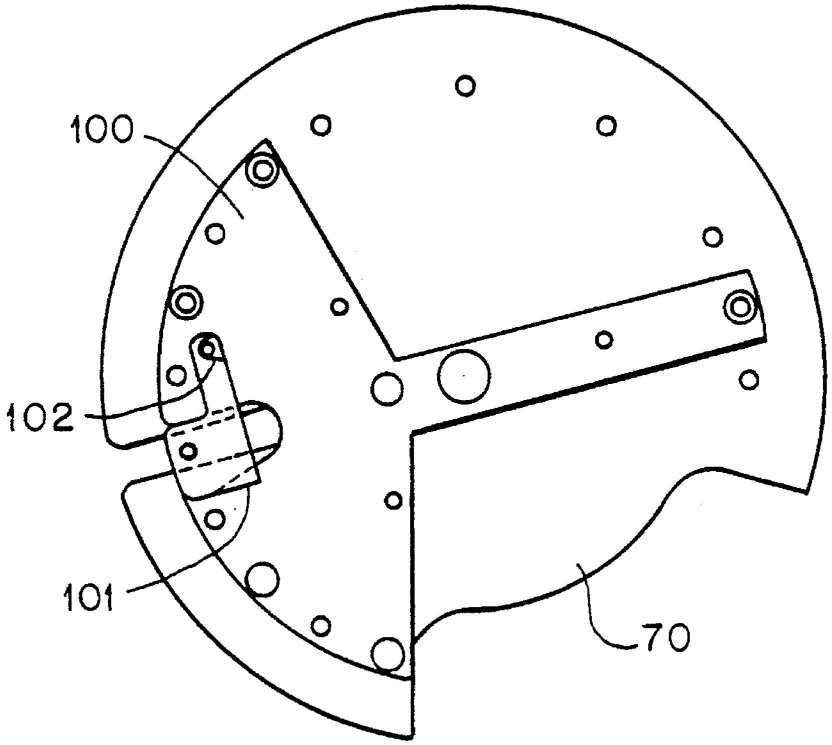
FIG. 7 is a top view of a pressure head and nozzle support rack utilized with the apparatus illustrated in FIG. 1.

FIG. 7 is a top view of nozzle support rack 100 and pressure head 70. As shown in FIG. 7, the nozzle support rack 100 is disposed for rotation about the same central axis as the pressure head 70 in a manner which allows the nozzle support rack 100 to rotate relative to pressure head 70.

Pressure head 70 is also designed for vertical movement relative to both the nozzle support rack 100 and the column transport disc 40 which do not move in the vertical direction. The vertical spacing between nozzle support rack 100 and transport disc 40 is maintained by a number of positioning pins 115 which are fixed to the bottom of the nozzle transport rack 100. Positioning pins 115 pass through holes in pressure head 70 and slide freely across the top of column transport disc 40.

With reference to FIGS. 13 and 14 which illustrate the vertical movement of pressure head 70, reagent nozzles 105 are rigidly attached to nozzle support rack 100. Reagent is supplied to each reagent nozzle 105 through an intake 106 from an independent source of reagent (not shown) which is preferably metered to the reagent dispense nozzle 105 by a precision pump. Reagent is delivered from a bottom orifice 107 of reagent nozzle 105 when reagent nozzle 105 is in the DISPENSE position as shown if FIG. 13.

A pressure head 70, preferably in the form of a disc identical in diameter to the transport disc 40, is disposed in position parallel to the transport disc 40. As shown in FIG.

7, the contour of the pressure head disc 70 is modified so that its radius is decreased for a segment of its circumference to avoid interference with other components at task stations one, eleven and twelve.

When it is desired to supply a pressurized gas to a sample preparation column 50, pressure head 70 is lowered to the PRESSURIZE position which aligns a pressurization nozzle 75 over sample preparation column 50, as shown in FIG. 14. In order to insure that pressurization occurs, a gasket 72 is secured to the underside of pressure head disk 70 to create a fluid tight seal between pressure disk 70 and the sample preparation column 50. The gasket surrounding pressurization nozzle 75 may be in the form of a single strip which serves as a gasket for all of the pressurization nozzles 75 or may be comprised of a number of separate gaskets which each provide a seal for only one pressurization nozzle 75. The strip may be formed of any suitable material, such as a cellular urethane.

The pressure head 70 is lowered and rotated to bring gaskets 72 into contact with the tops of the sample preparation columns 50. The vertical control of the pressured head disc may be achieved in any fashion which does not interfere with other operations of the sample preparation apparatus. For example, the pressure head 70 may be fixed to a flanged nut having threads which cooperate with threads on a central rotatable shaft. In this manner, the vertical position of pressure head 70 can be easily controlled by controlling the bi-directional rotation of the shaft.

As shown in FIG. 13, when the pressure head 70 is in the DISPENSE position, the pressurized gas nozzle 75 is not aligned with a sample preparation column 50. In order to align pressurized gas nozzle 75 with column 50, pressure head 70 is lowered and rotated thereby causing the pressurized gas nozzle 75 to shift 15 degrees to a position over the column 50. The raising and lowering of pressure head 70 may be accomplished in any suitable manner, such as with a helically grooved connection between a central support shaft and the pressure head 70. In order to effect the rotation of pressure head 70 relative to nozzle support rack 100, a guide pin 102 extends from the pressure head 70 and passes through a clearance bore in the nozzle support rack 100. The top of guide pin 102 engages the bore of a swivel link 114, the pivot point 113 of which is fixed to a part of the apparatus structure. The guide pin 102 is configured with a collar 103 which engages the swivel link 114 as the pressure head 70 moves vertically. The swivel link 114 descends through an arc as long as the collar 103 remains in contact with the swivel link 114. The particular geometry of the swivel link 114 as it interacts with the guide pin 102 and collar 103 causes the guide pin to shift closer to pivot point 113 to the dispense position shown in FIG. 14. This lateral shift of guide pin 102 causes pressure head disc 70 to rotate 15° allowing the reagent dispense nozzles 105 at each of stations 2, 3, 4, 5, 6 and 10 to align over a column 50 for the dispensing of reagent.

According to a test procedure control and monitoring sequence which has been previously selected, a reagent can be transferred, by way of a precision metering pump from a reagent supply vessel , through an appropriate conduit 106, to a reagent dispense nozzle 105 in position over a column. After having dispensed an appropriate volume of reagent into the column, the metering pump is stopped.

Dispense nozzles 75, 105, through which pressurized gas or a reagent can be directed into a column paused at a task station, are inserted through penetrations in the pressure head disc 70 and gasket strip 72. Those skilled in the art will appreciate that it may be desirable to provide each task station with either a pressurized gas dispense nozzle 75 only, a reagent dispense nozzle 105, or both a pressurized gas dispense nozzle 75 and a reagent dispense nozzle 105 depending upon the particular function assigned to that task station.

It will therefore be understood that reagents and/or pressurized gasses can be selectively dispensed to the sample preparation columns at various stations along the transport path while maintaining separation between reagents and pressurizing gases.

As a column is indexed from task station one to task station two, the pressure head 70 is raised to provide clearance for the column. During the INDEX the radial alignment of the pressure head 70 is held in the DISPENSE position. If the test procedure requires the dispensing of a pressurized gas into the column at task station two, the control and monitoring system will provide a signal to shift the radial alignment of the pressure head 70 to the PRESSURIZE position. Once this SHIFT has been completed and verified by an opto-electrical sensor (not shown) positioned to monitor performance, the pressurization portion of the preparation procedure is begun.

Figure 8:
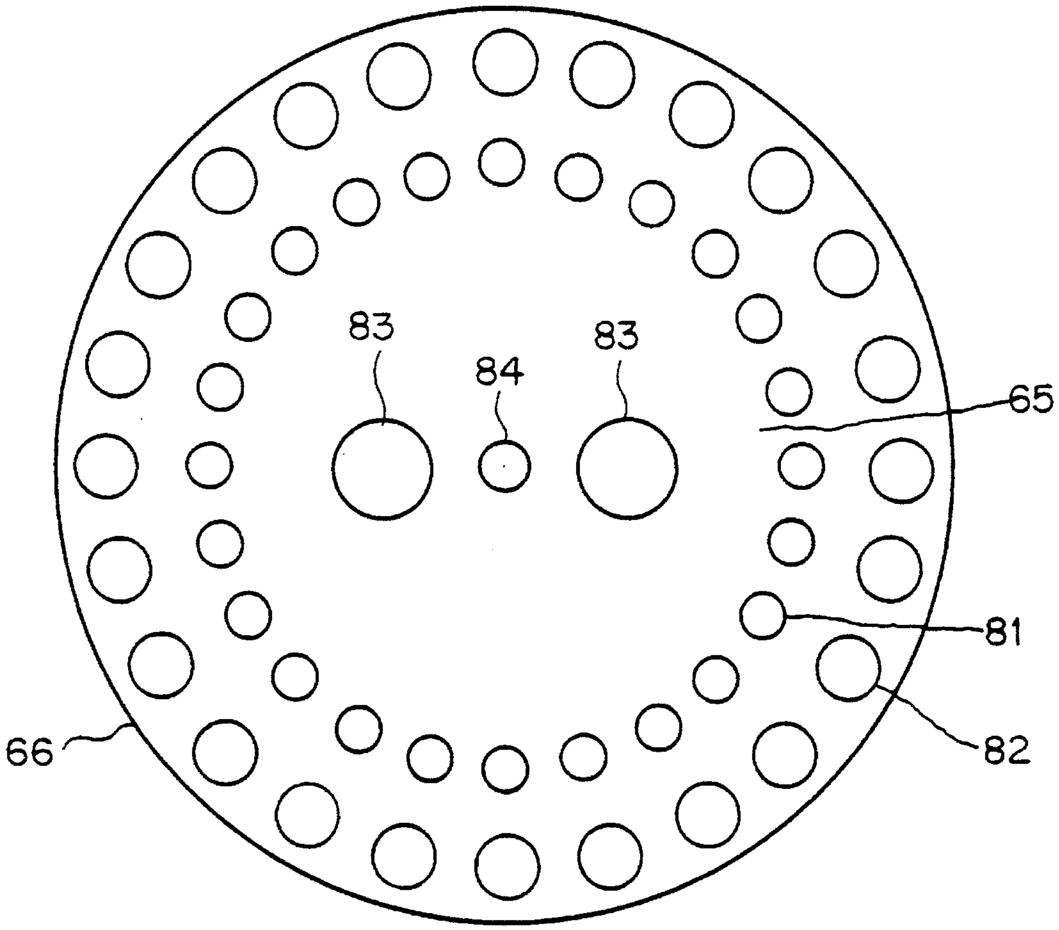
FIGS. 8 and 9 are top and side views respectively, of a specimen/tip carousel utilized with the apparatus illustrated in FIG. 1.
Figure 9:
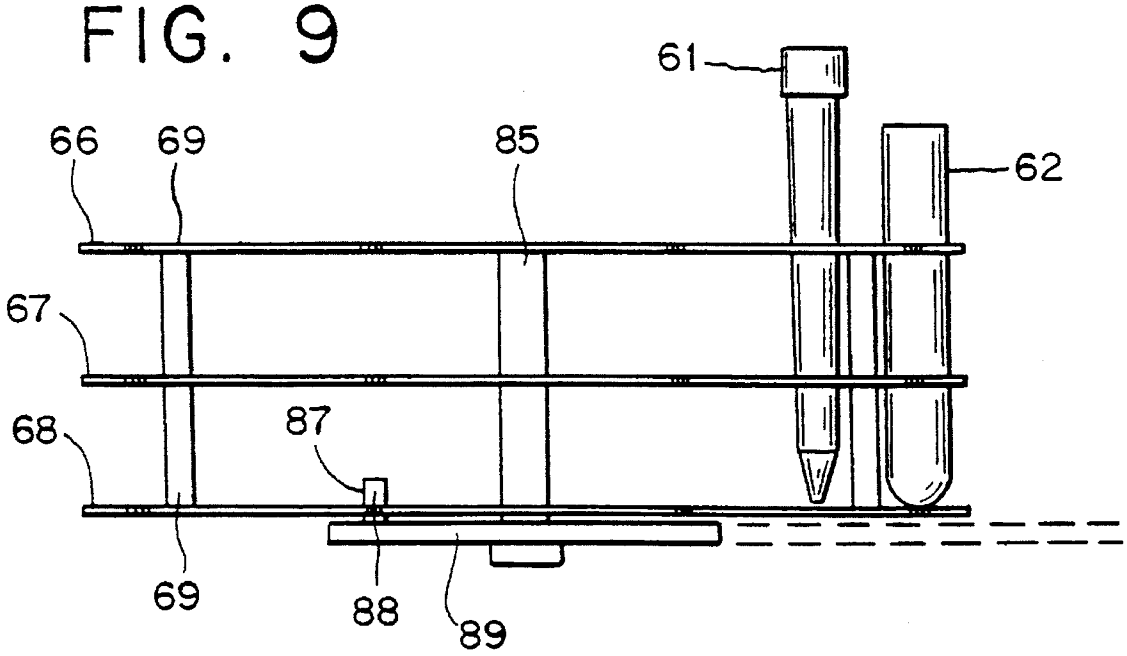

At the beginning of a sample preparation procedure, a specimen/tip carousel 65 as shown in FIGS. 8 and 9, having a number of receptacles, for example twenty-four, dimensioned to receive specimen containers 62 and disposable transfer tips 61 is loaded with the desired number of test specimen containers 62 and a corresponding number of disposable transfer tips 61. The illustrated specimen/tip carousel 65 consists of three discs 66,67,68, preferably formed of a durable, corrosion resistant material, for example polypropylene. The discs are held together, with their center points in vertical alignment, by spacers 69 fastened between them, near their perimeters. The bores 81 which carry the disposable transfer tips 61 are arranged on a reference circle having a radius slightly less than the reference circle on which the specimen containers are arranged thereby placing each test specimen container bore 82 next to its corresponding disposable transfer tip bore 81 and on a single radial line. These paired bores are preferably cut into both the upper most disc and the intermediate disc in vertical alignment. The lengths of the spacers 69 are arranged so that as the bottom of a test specimen container 62 rests in contact with the lower most disc 68 the bore of the intermediate disc 67 will cradle test specimen container 62 near is mid-height and the bore of the upper most disc 66 will cradle the upper portion of the test specimen container 62. This arrangement insures that the test specimen containers 62 will remain vertical throughout the entire preparation procedure. Similarly, the disposable pipette tips 61 are held vertical throughout a procedure.

Additional bores 83 in the upper most disc 66 of the test specimen/tip carousel 65 act as finger holes to ease handling by laboratory personnel. Each of the three discs is further configured with a center bore 84 which, during the preparation procedure, engages a spindle 85. The spindle 85, which is fixed to a part of the structure, serves to locate the tip/specimen container carousel 65 in its proper synchronization with other elements of the invention during the preparation procedure. The lower most disc 68 of the test specimen/tip carousel 65 has one additional bore 87. This additional bore 87 is adapted to engage a locator pin 88 on a rotatable support 89 which acts as a reference point to insure the proper initial placement of the test specimen/tip carousel 65.

Figure 2:
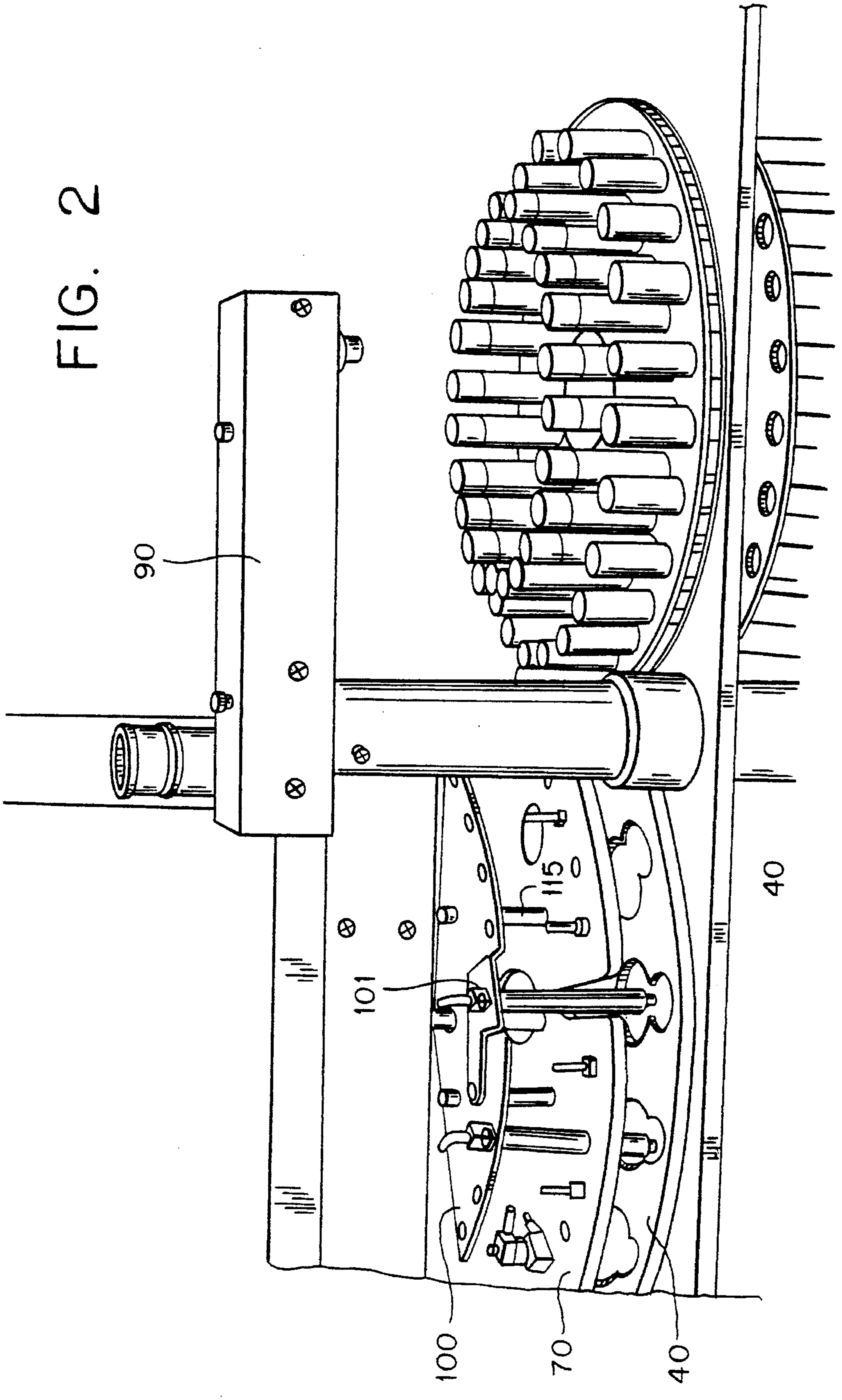
FIG. 2 is a partial, rear perspective view of the transfer arm, test specimen/tip carousel, column carousel and column feeder of the embodiment shown in FIG. 1.

Test specimen is transferred to a column 50 at task station four. Task station four is similar in function to task stations two and three in that it has both a reagent dispense nozzle 105 and a pressurized gas dispense nozzle 75. The form of the reagent dispense nozzle 105 is modified, however, to permit it to retract from its dispensing position when specimen is delivered to a column 50. The particular reagent dispense nozzle 105 positioned at task station 4 is mounted on a biased, pivoting support 101 illustrated, in FIGS. 2 and 7, which is secured to nozzle support rack 100. Pivoting support 101 allows the displacement of the dispense nozzle 105 at task station 4 providing clearance for the insertion of disposable specimen transfer tip 61 used during the specimen transfer sequence. Displacement of the dispense nozzle 105 is accomplished when transfer tip 61 attached to the transfer arm assembly 90 engages the pivoting support 101 of the nozzle support rack 100 during rotation of the transfer arm. Alternatively, a cam may be attached to the transfer arm assembly 90 to minimize the risk of dislodging a transfer tip. The return of the nozzle is readily accomplished using a simple leaf spring 102.

Figure 10:
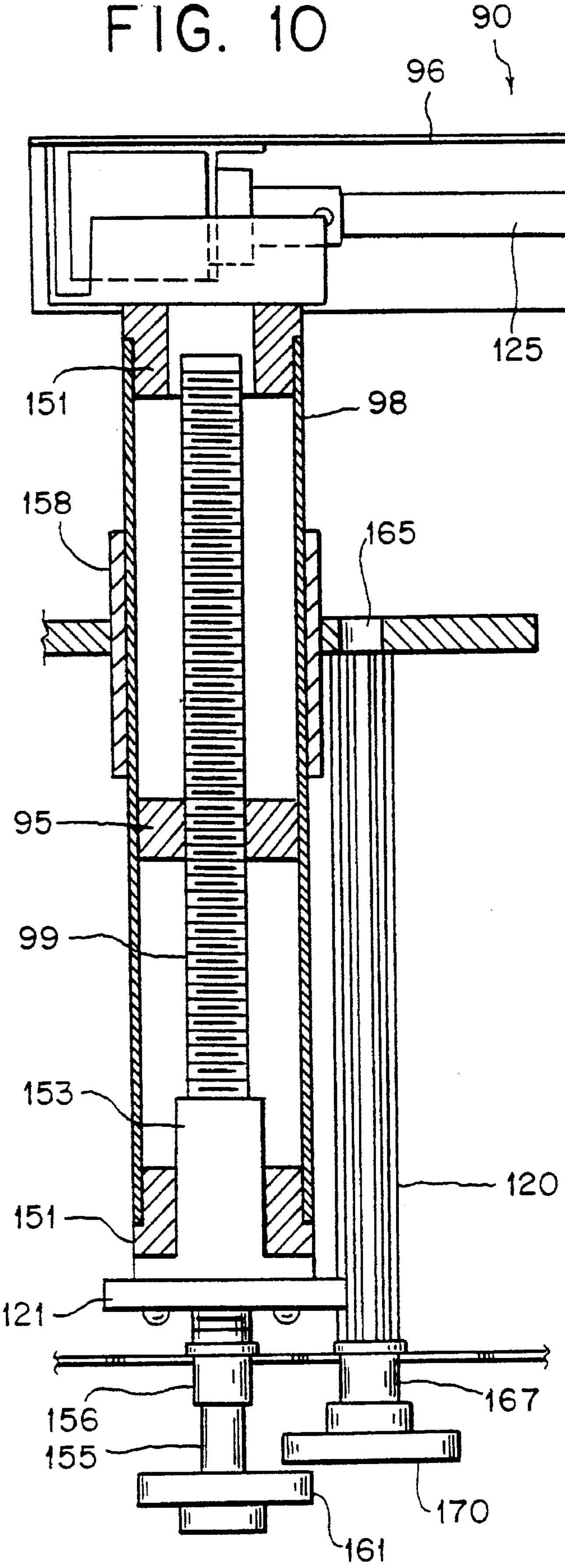
FIG. 10 is a cross-sectional, side view of a transfer arm utilized with the apparatus illustrated in FIG. 1.
Figure 11:
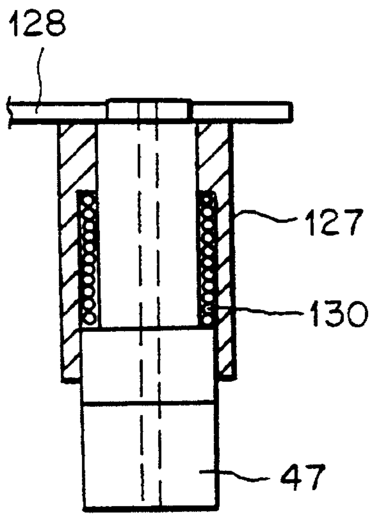
FIG. 11 is a cross-sectional, side view of a transfer arm tip ejector utilized with the apparatus illustrated in FIG. 1.

The test specimen transfer assembly 90 of the illustrated embodiment shown in FIGS. 10 and 11, comprises a transfer arm 96 having a tapered stopper 97. The transfer arm 96 is mounted on a support 98 which can be raised and lowered as desired as well as rotated about an elevating shaft 99. The tapered stopper 97 is adapted to frictionally engaged a disposable transfer tip 61 when the stopper 97 is lowered into the disposable tip. The stopper 97 is designed to form an interference fit with the disposable tip thereby allowing transfer arm 96 to raise the tip out of transfer tip/specimen carousel 65 and utilize that tip for the transfer of specimen from a specimen container 62 to a sample preparation column 50. The rotation and vertical movement of center support tube 98 is readily accomplished using a threaded elevating shaft 99 which is readily attached to center support tube 98 with a bushing 95. From the illustration in FIG. 10, it will be appreciated that when elevating shaft 99 is rotated within bushing 95, the center support tube may be raised or lowered as desired. The rotation of transfer arm 96 is readily accomplished with a pinion 120 adapted to engage a gear 121 disposed on the circumference of center support tube 98. By suitably controlling both elevating shaft 99 and pinion 120, the transfer arm 96 can be raised, lowered and rotated about an axis defined by elevating shaft 99 as desired in order to effect the transfer of a test specimen. The illustrated apparatus thereby advantageously provides a test specimen transfer assembly 90 which moves a disposable transfer tip 61 along a path between a specimen container 62 and a sample preparation column 50 which does not pass over another specimen container or another sample preparation column.

Transfer arm 96 is also advantageously provided with an internal conduit 125 which extends through transfer arm 96 and down through tapered stopper 97. The other end of conduit 125 is attached to a reversible, precision metering pump (not shown). The reversible, precision metering pump is energized when a disposable tip is lowered into a specimen container in order to draw specimen into the disposal tip. The action of the reversible, precision metering pump is then reversed to discharge the test specimen into a sample preparation column after the transfer arm 96 has been rotated to properly align the disposable tip over the opening of a column.

The suction applied to the disposable tip 61 is carefully controlled such that a specimen is only drawn into the disposable tip and does not reach tapered stopper 97 in order to avoid contamination between test specimens. The transfer of a test specimen from a specimen container 62 in the test specimen/tip carousel 65 into the column 50 in position at task station four is accomplished by the test specimen transfer assembly 90.

After the transfer of a test specimen, an ejection mechanism 127 is energized to eject a used disposable tip 61 from tapered stopper 97. The ejection mechanism 127 may be in the form of a slidable sleeve attached to a spring 130 and electric actuator having sufficient force to dislodge a disposable tip. The slidable sleeve is connected, by way of a lever 128 and suitable linkage 129, to an electric actuator (not shown). Upon receiving a signal from the control and monitoring system, the actuator and linkage 129 will bring the lever 128 to bear downwardly on the slidable sleeve and consequently exert substantial force on the rim of the disposable tip 61. It is in this manner that the disposable tip 61 can be ejected after the transfer of a test specimen. The ejected disposable tip is preferably carried by a chute to a disposal bin 450 located beneath the sample preparation area as shown in FIG. 17. The transfer arm 96 is then rotated to its home position. Upon rotation of the transfer tip, test specimen carousel aligns another disposable tip and test specimen container with tapered stopper 97.

The DISPENSE and PRESSURIZE portions of the preparation procedure are resumed according to the test control and monitoring sequence.

Figure 12:
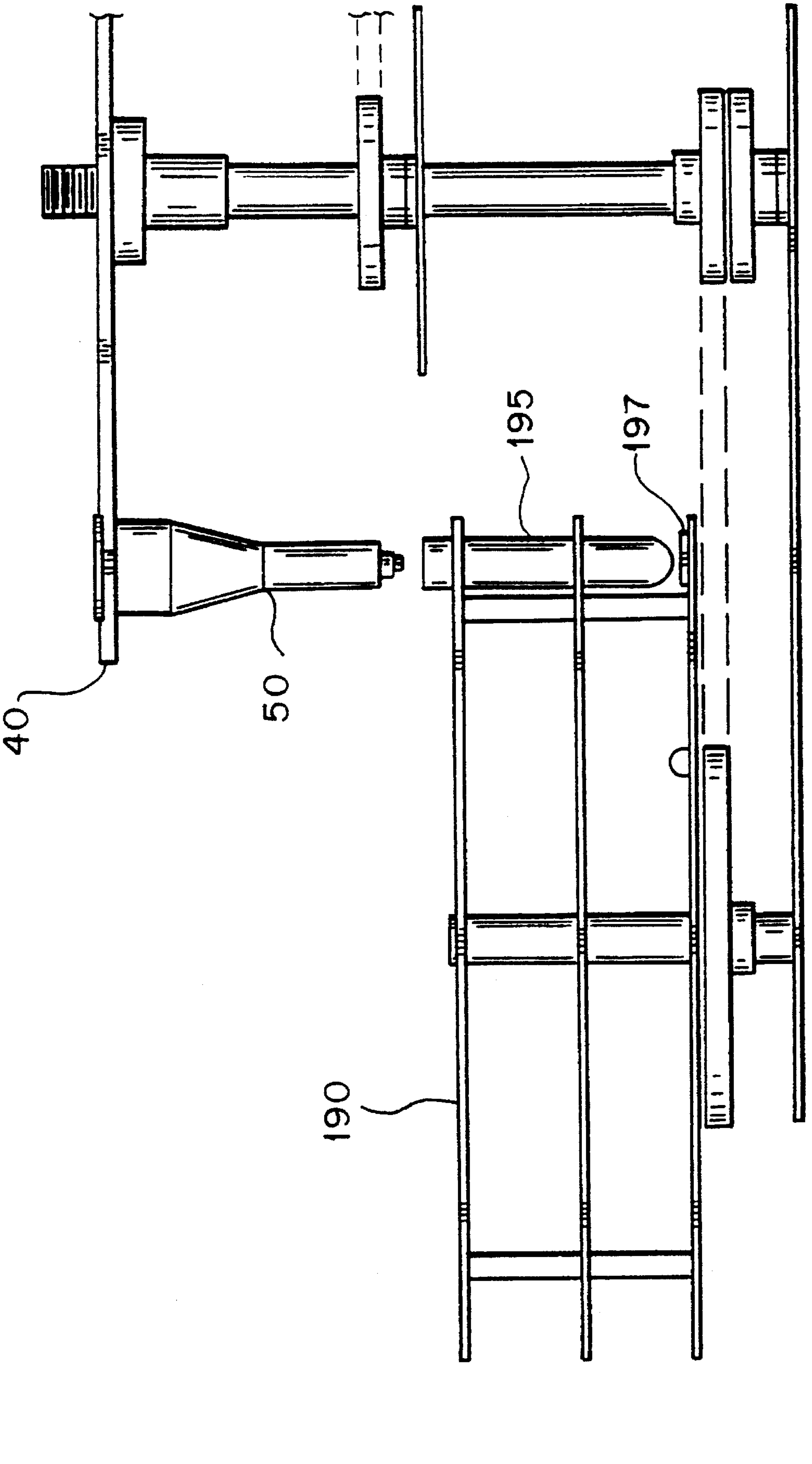
FIG. 12 is a side view of a collection tube and collection carousel shown positioned relative to a column in a transport disc.

Task station four may also be equipped to collect the effluent being discharged from the outlet port of the column. In the illustrated embodiment, an eluate collection rack 190 is provided. The eluate collection rack 190 shown in FIG. 12 has essentially the same configuration as the test specimen/tip carousel 65, but collection rack 190 is designed to position collection tubes 195. Any suitable mechanism can be utilized to rotate the collection rack 190 and thereby position collection tubes 195 as required. In order to enhance the drying of the eluate collection tubes 195, a small electrical resistance heater 197 may be positioned below each collection tube 195. The flow of electricity through the heater 197 is also advantageously controlled through central processing unit 10.

Task stations five and six are identical in form and function to task stations two and three. If the test procedure requires a reagent to be dispensed at task station five and/or six, the DISPENSE, SHIFT and PRESSURIZE sequences are repeated after the test specimen transfer is completed. The columns at task stations two, three, four, five and six are processed simultaneously while a new column is entering transport at task station one.

Task stations seven, eight and nine of the illustrated embodiment only have a pressurized gas dispense nozzle. In order to enhance the drying of the adsorbent media within each column, pressurized gas can be directed into the columns at each of these task stations. Since these task stations have no reagent dispense nozzles assigned to them, the columns at these stations are simply left idle while the pressure head 70 is shifted to the DISPENSE position. A two position flow control valve (not shown) is advantageously positioned in the gas conduit supplying each of the pressurized gas dispense nozzles 75 to start and stop the flow of pressured gas once the pressure head 70 has returned to the PRESSURIZE position. Any effluent being discharged from columns at these task stations is diverted to waste.

Task station 10 is equipped with a reagent nozzle 105 to dispense reagent into the column and with a pressurized gas dispense nozzle 75 to pressurize the column. Task station ten also has an eluate collection container rack 190 with collection containers 195, similar to the collection rack 190 shown in FIG. 12, to collect eluate at task station ten. Other embodiments of the present invention can be provided with eluate collection containers 490 at other task stations as well as shown in FIG. 17.

In order to reduce the time required for drying the eluate collected in containers 195, a heated gas, such as air, can be directed into the containers 195. For example, as shown in FIG. 1, three retractable nozzles 170 are positioned over the eluate containers 195 to direct hot air into containers after they have rotated out from under the apparatus support structure. The retractable nozzles 170 are controlled by central processing unit 10 so that they are retracted when eluate collection container rack 190 is rotating. Alternatively, the retractable nozzles 170 may be connected to a vacuum (not shown) in order to draw vapor from the collection containers 195. Such a vacuum can be used alone or in combination with the heating element 197 described above.

Figure 15:
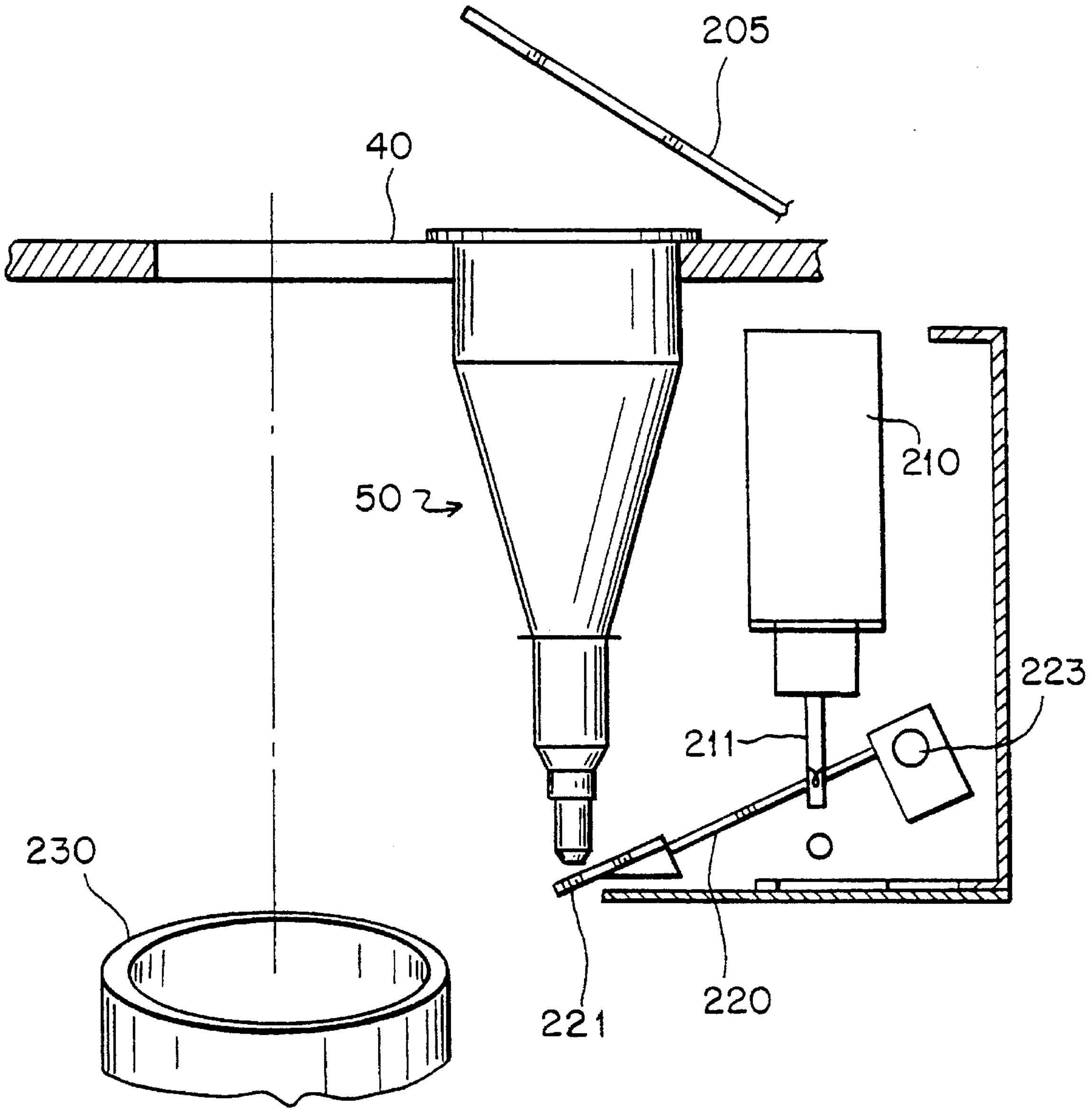
FIG. 15 is a column ejector mechanism of the embodiment illustrated in FIG. 1.
Figure 16:
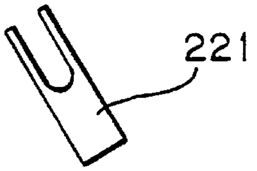
FIG. 16 is a top view of a forked member used with one embodiment of an ejection member of the present invention.

Task station eleven is equipped with a column eject mechanism, illustrated in FIG. 15, which serves to eject the used column which has exited task station ten, and to pass that column to a disposal chute 230 which directs the column 50 to a disposal bin located beneath the instrument. The column eject mechanism is designed to lift a column 50 which is supported by the minor diameter support section 44 of transport disc 40 and direct the column to the major diameter release section 45. To accomplish this, column eject mechanism is provided with a pivoting forked manipulator 220 which is attached to an electric actuator 210. The actuator 210 comprises a rod 211 which moves substantially upwardly when the actuator 210 is actuated. When actuated, the rod 211 causes the forked manipulator 220 to pivot around pivot point 223 and engage the spent column 50. The non-pivoting end of forked manipulator 220 is provided with a forked member 221 for engaging the lower end of a column 50. Thc configuration of forked member 221 of this embodiment of the present invention is best shown in the top view of FIG. 16. In this manner, the spent column is raised upwardly, out of minor diameter support region 44 of compound bore 43 and into major diameter release region 45. An inclined guide surface 205 is advantageously positioned above the spent column 50 at task station eleven in order to guide the upwardly moving column 50 toward release region 45. A disposal chute 230 is positioned below release region 45 in order to guide the spent columns into a disposal bin (not shown) which is removable located in the bottom of the instrument.

When continuous operation over an extended period is desired, the present invention offers laboratory personnel the option of continuously feeding new specimen containers, clean disposable transfer tips, and eluate collection containers, while removing used specimen containers and full eluate collection containers. With reference to FIG. 1, additional transfer mechanisms 290 and 390 which are operable in a manner similar to transfer mechanism 90, are provided to transfer the aforesaid tips and containers to and from remote carousels, such as carousel for 460, when desired.

Another aspect of the present invention that is advantageous in laboratory environments is that the entire apparatus is operated with voltages not exceeding 24 volts. Therefore, the risk of electrical mishaps or explosion when working with flammable solvents is minimized.

The present invention thus provides higher test procedure quality while reducing laboratory overhead allowing a single lab technician to perform the same number of test procedures as several lab technicians working manually over the same given time.

What is claimed is:

1. An apparatus for automatically separating at least one compound from a plurality of discrete liquid specimens comprising:

a plurality of sample preparation columns, each of said columns comprising an upper inlet port, a lower outlet port, and means for removing at least one compound from a fluid specimen disposed inside said column, each of said sample preparation columns further comprising a flange having an outer diameter and a sidewall proximately disposed below said flange, said sidewall having an exterior diameter less than said outer diameter of said flange;

a plurality of specimen containers holding discrete liquid specimens wherein each specimen container holds one of said liquid specimens;

a plurality of disposable specimen transfer tips for transferring discrete aliquots of specimen from said specimen containers to said sample preparation columns;

means for engaging said disposable transfer tips wherein said engaging means draws specimen from a specimen container into a disposable tip, positions said disposable tip proximate one of said sample preparation columns and dispenses said specimen into said sample_preparation column;

a plurality of reagent dispense stations;

means for transporting said sample preparation columns to said plurality of reagent dispense stations said transporting means connected to said dispense stations and said engaging means;

said transporting means comprising a support member having a plurality of compound bores, each of said compound bores comprising a support region having a first diameter smaller than said outer diameter and greater than said exterior diameter for supporting one of said sample preparation columns in a vertical orientation and a release region having a second diameter greater than said outer diameter of said flange and for allowing one of said sample preparation columns to fall through said compound bore and from said transporting means wherein said compound bores comprise means for preventing said sample preparation columns from sliding from said support region to said release region.

2. An apparatus for automatically separating at least one compound from a plurality of discrete liquid specimens according to claim 1 further comprising means for ejecting said sample preparation columns from said transporting means wherein said ejecting means moves at least one of said sample preparation columns from said support region of one of said compound bores to said release region.

3. An apparatus for automatically separating at least one compound from a plurality of discrete liquid specimens according to claim 2 wherein said ejecting means causes said sample preparation column to move upwardly before moving said column to said release region.

4. An apparatus for automatically separating at least one compound from a plurality of discrete liquid specimens according to claim 1 further comprising an automatic column feeder comprising:

a column support comprising a plurality of columns arranged in vertical, overlapping relation; and means for selectively releasing one of said columns into said support region of one of said compound bores of said transporting means.

5. An apparatus for automatically separating at least one compound from a plurality of discrete liquid specimens according to claim 4 wherein said column support comprises a removable hollow cylinder.

6. An apparatus for automatically separating at least one compound from a plurality of discrete liquid specimens according to claim 4 wherein said column support is transparent.

7. An apparatus for automatically separating at least one compound from a plurality of discrete liquid specimens according to claim 4 wherein said releasing means comprises at least two independently movable, electric actuators.

8. An apparatus for automatically separating at least one compound from a plurality of discrete liquid specimens according to claim 7 wherein said releasing means further comprises at least one arcuate support member having a diameter substantially equal to said first diameter of said support region.

9. An apparatus for automatically separating at least one compound from a plurality of discrete liquid specimens according to claim 1 further comprising:

a pressure head movably mounted above said transporting means for movement in both the vertical and horizontal directions;

a plurality of pressurized gas dispensers disposed on said pressure head for delivering pressurized fluid to said sample preparation columns;

wherein said pressure head is selectively moveable from a first position where a pressurized gas dispenser is aligned with an inlet port at a reagent dispense station to a second position where said pressurized gas dispenser is not aligned with said inlet port.

10. An apparatus for automatically separating at least one compound from a plurality of discrete liquid specimens according to claim 9 further comprising:

at least one sealing member having a resilient, surface for providing a fluid-tight seal between at least one of said pressurized gas dispensers and an inlet port of a sample preparation column.

11. An apparatus for automatically separating at least one compound from a plurality of discrete liquid specimens according to claim 10 wherein said sealing member is attached to said pressure head.

12. An apparatus for automatically separating at least one compound from a plurality of discrete liquid specimens according to claim 10 wherein said sealing member is substantially planar.

13. An apparatus for automatically separating at least one compound from a plurality of discrete liquid specimens according to claim 10 comprising a plurality of sealing members wherein each of said sealing members is positioned proximate one of said pressurized gas dispensers.

14. An apparatus for automatically separating at least one compound from a plurality of discrete liquid specimens according to claim 9 further comprising a nozzle support rack and a plurality of reagent nozzles disposed on said nozzle support rack for dispensing reagent to said sample preparation columns.

15. An apparatus for automatically separating at least one compound from a plurality of discrete liquid specimens according to claim 14 further comprising a linking member for coordinating movement between said nozzle support rack and said pressure head whereby only one of said pressurized gas dispensers or one of said reagent nozzles are aligned with one inlet port at any given time.

16. An apparatus for automatically separating at least one compound from a plurality of discrete liquid specimens according to claim 1 further comprising a computer control unit.

17. An apparatus for automatically separating at least one compound from a plurality of discrete liquid specimens according to claim 16 wherein said apparatus comprises drive mechanisms for said transfer tip feed mechanism and said transporting means which operate at voltages not exceeding 24 volts.

18. An apparatus for automatically separating at least one compound from a plurality of discrete liquid specimens according to claim 1 further comprising a transfer tip carousel and a transfer tip feed mechanism for automatically delivering disposable specimen transfer tips to said transfer tip carousel.

19. An apparatus for automatically separating at least one compound from a plurality of discrete liquid specimens comprising:

a plurality of sample preparation columns, each of said columns comprising an upper inlet port, a lower outlet port, and means for removing at least one compound from a fluid specimen disposed inside said column;

a plurality of specimen containers holding discrete liquid specimens wherein each specimen container holds one of said liquid specimens;

a plurality of disposable specimen transfer tips for transferring discrete aliquots of specimen from said specimen containers to said sample preparation columns;

means for engaging said disposable transfer tips wherein said engaging means draws specimen from a specimen container into a disposable tip, positions said disposable tip proximate one of said sample preparation columns and dispenses said specimen into said sample preparation column;

a plurality of reagent dispense stations;

means for transporting said sample preparation columns to said plurality of reagent dispense stations said transporting means connected to said dispense stations and said engaging means;

a pressure head movably mounted above said transporting means for movement in both the vertical and horizontal directions;

a plurality of pressurized gas dispensers disposed on said pressure head for delivering pressurized fluid to said sample preparation columns;

wherein said pressure head is selectively moveable from a first position where a pressurized gas dispenser is aligned with an inlet port at a reagent dispense station to a second position where said pressurized gas dispenser is not aligned with said inlet port and wherein said pressure head is helically connected to a central support shaft such that vertical movement of said pressure head causes said pressure head to rotate relative to said transporting means.

20. An apparatus for automatically separating at least one compound from a plurality of discrete liquid specimens according to claim 19 further comprising a plurality of collection vessels disposed in a movable collection vessel support which is selectively moveable to position a collection vessel below an outlet port of one of said sample preparation columns to collect fluid existing said outlet port at a dispense station.

21. An apparatus for automatically separating at least one compound from a plurality of discrete liquid specimens according to claim 20 comprising a plurality of said collection vessel supports movably disposed for collecting fluids at a plurality of said dispense stations.

22. An apparatus for automatically separating at least one compound from a plurality of discrete liquid specimens according to claim 20 further comprising means for drying said collection vessels.

23. An apparatus for automatically separating at least one compound from a plurality of discrete liquid specimens according to claim 22 wherein said drying means comprises means for heating said collection vessels.

24. An apparatus for automatically separating at least one compound from a plurality of discrete liquid specimens according to claim 23 wherein said heating means comprises at least one electrical resistance heating element.

25. An apparatus for automatically separating at least one compound from a plurality of discrete liquid specimens according to claim 22 wherein said drying means comprises means for removing vapor from said collection vessels.

26. An apparatus for automatically separating at least one compound from a plurality of discrete liquid specimens according to claim 25 wherein said vapor removing means comprises at least one exhaust tube disposed proximate a collection vessel and a vacuum generator connected to said suction tube whereby vapor is drawn from said collection vessel into said exhaust tube.

* * * * *